United States Patent

Keshelava

[11] Patent Number: 5,413,601
[45] Date of Patent: May 9, 1995

[54] TUBULAR ORGAN PROSTHESIS

[76] Inventor: Viktor V. Keshelava, ulitsa Akademika Chelomeya, 4, kv, 20, Moscow, U.S.S.R.

[21] Appl. No.: 128,735

[22] Filed: Sep. 30, 1993

Related U.S. Application Data

[63] Continuation of Ser. No. 776,341, Nov. 22, 1991, abandoned.

[30] Foreign Application Priority Data

Mar. 26, 1990 [SU] U.S.S.R. .................. 4827536

[51] Int. Cl.⁶ .......................... A61F 2/04; A61F 2/20
[52] U.S. Cl. .............................. 623/12; 623/11; 623/1; 623/9
[58] Field of Search ............... 623/9, 12, 1, 11; 604/282, 283

[56] References Cited

U.S. PATENT DOCUMENTS

| | | |
|---|---|---|
| 4,345,414 | 8/1982 | Bornat et al. ............. 623/1 X |
| 4,583,969 | 4/1986 | Mortensen ............... 623/9 X |
| 4,681,570 | 7/1987 | Dalton ..................... 604/282 |
| 4,728,328 | 3/1988 | Hughes et al. . |
| 4,747,848 | 3/1988 | Maini . |
| 4,820,298 | 4/1989 | Leveen et al. ............. 623/1 |
| 4,911,689 | 3/1990 | Hattler ..................... 604/24 |
| 5,092,886 | 3/1992 | Dobos-Hardy .......... 623/12 |

FOREIGN PATENT DOCUMENTS

| | | |
|---|---|---|
| 144534 | 6/1985 | European Pat. Off. . |
| 0201667 | 11/1986 | European Pat. Off. ..... 623/1 |
| 2811372 | 11/1978 | Germany ................ 623/12 |
| 4104702 | 8/1992 | Germany ................ 600/30 |
| 1479002 | 7/1977 | United Kingdom ...... 623/12 |
| WO87/05796 | 10/1987 | WIPO . |

OTHER PUBLICATIONS

Obzornaya informatsia, Meditsina i zdravookharenie No. 6.

Primary Examiner—David H. Willse
Attorney, Agent, or Firm—Keck, Mahin & Cate

[57] ABSTRACT

The tubular organ prosthesis (1) of the invention is prepared from a prosthesis of a vessel (2) which is made up of an outer surface (3) facing tissues and an inner surface covered with an epithelium surface (4) of a wall (5) of the tubular organ. The wall (5) is isolated from the surrounding medium.

8 Claims, 4 Drawing Sheets

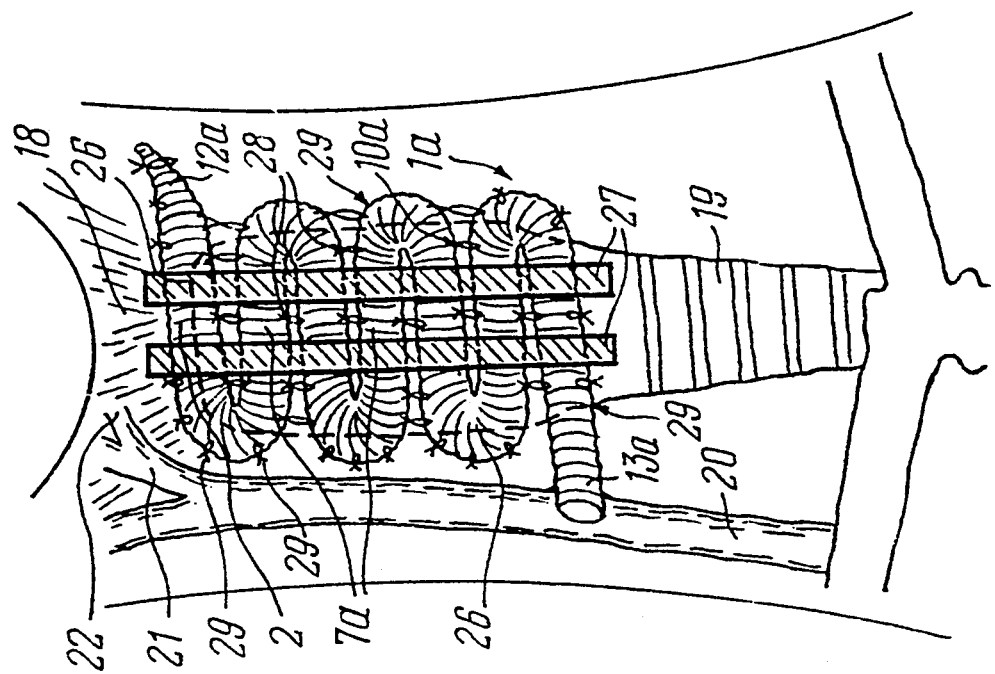
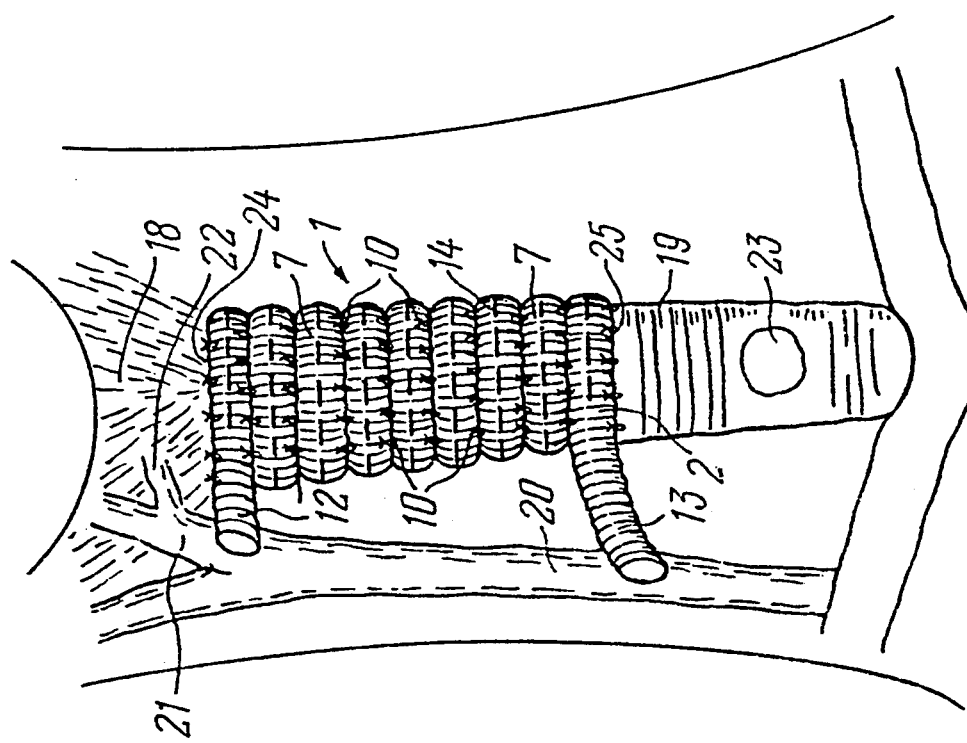

TUBULAR ORGAN PROSTHESIS

This is a continuation application of Ser. No. 07/776,341, filed on Nov. 22, 1991, now abandoned.

FIELD OF THE INVENTION

The present invention relates to medicine, specifically to a tubular organ prosthesis.

This invention can be used most advantageously in prosthetics for the larynx, trachea, bronchi and esophagus. It can be used successfully in reconstructive-restorative surgery of the bile and urinary ducts and vagina.

PRIOR ART

The last 20–25 years were marked by a considerable prevalence of tumorous diseases of various organs, especially of the respiratory, gastrointestinal and genitourinary organs. The present methods for treating inflammatory diseases of the above organs result, in a number of cases, in development of cicatricial changes that subsequently require complex reconstructive-restorative surgery. As a rule, only rather limited organ affections are eliminated by reconstructive operations. In such cases the ends of the resected organ are sutured to each other to reconstruct the integrity of the organ operated on. If the lesion is considerable, the need arises in its resection for prosthetics.

More comprehensive organ resection requires prosthetics. The biological auto- and allotransplants that have been tested by the present time failed to produce the desirable results. This was due to serious complications such as suppuration and prosthesis rejection in different postoperative terms. These disadvantages are very grave and inherent in the majority of the implanted prosthesis, hence impetus was given to the development of biologically compatible prostheses implantable in the recipient's body.

Research into this field has led to the creation of the most suitable, from the clinical standpoint, tubular organ prosthesis (U.S. Pat. No. 4,728,327), e.g., tracheal prosthesis.

The known prosthesis comprises a tubular based made of a hemocompatible polymer material and cuffs each of which is formed at the ends of the tubular base. The prosthesis tubular base and each cuff make up a singular element.

Although a special material has been selected which provides for the prosthesis to have biological inertness in the body and the prosthesis inner surface has been made smooth, promoting mucus secretion from the distal part of the bronchial tree, epithelization of the inner surface has not taken place. The latter circumstance is caused by the lack of blood supply to the prosthesis owing to its monolithic properties which hinders tissue intergrowth in its walls—the indispensable condition set for a tracheal prosthesis.

Attempts at making a prosthesis with a porous surface that promotes its intergrowth with the body's tissues and is capable of epithelization has promoted the creation of the tubular organ prosthesis made from a prosthesis of the vessel (Bulletin of the All-Union Research Institute of Medical and Medico-Technical Information of the USSR Ministry of Health, No. 8, 1988, December, Moscow, M. I. Perelman, Ju. V. Birjukov, N. S. Koroleva, et al., "Tracheal Prosthesis", p. 1-42, see p. 20).

The known prosthesis of the vessel is a crimped Lavsan tube. To provide its elasticity, a metallic framework is fitted inside the tube.

Use of the above prosthesis in animal experiments, e.g., on dog trachea, demonstrated that despite sufficient elasticity and the network structure of the prosthesis that provides it with "host" tissue intergrowth, implantation and epithelization of the prosthesis inner surface did not occur, which gave rise to purulent granulation inflammation with subsequent prosthesis rejection.

DISCLOSURE OF THE INVENTION

It is an object of the invention to provide a tubular organ prosthesis whose construction would ensure blood supply to the prosthesis during the whole period of its functioning.

The object is attained by a tubular organ prosthesis, in accordance with the invention, in which the prosthesis of the vessel has an outer surface facing the tissues and an inner surface covered with epithelium of the tubular organ wall and has free ends one of which is intended for connection with an artery and the other, for compression for the period of filling the prosthesis with blood.

This structural arrangement of the tubular organ prosthesis provides for its blood supply within the whole period of its functioning. The continuous blood flow in the tubular organ prosthesis, made in accordance with the invention, promotes a metabolic process between the prosthesis wall and the tissues surrounding it to lead to its implantation and prevent development of an inflammatory process in the zone of prosthesis. The biological properties of blood that constantly circulates in the tubular organ prosthesis make the real basis for prosthesis implantation in the recipient's body and allows epithelization of its whole inner surface to prevent scars and anastomoses in the prosthesis zone. Functioning of the tubular organ prosthesis is not impaired due to its epithelization irradiation either before or after prosthesis application. The term of prosthesis functioning is determined by the state of the recipient's blood system in which the prosthesis becomes a constituent part.

The wall of the tubular organ prosthesis is isolated from the surrounding medium, i.e., air is prevented from passing through it in the recipient's tissue, and the tissue fluid and blood from getting in the cavity of the organ prosthesis, provides adequate prosthesis functioning during the ingrowth of its wall by the recipient's tissues. All the above conforms with the requirements set for the tubular organ prosthesis such as the absence of toxicity, biological inertness, sufficient drainage function for mucus discharge from the air passages, impermeability to air, fluid and bacteria, implantability and epithelization of its whole inner surface, which makes it use successful whatever the organ repaired by the prosthesis. Hence, the proposed construction of the tubular organ prosthesis can be used for making prostheses of the larynx, which is a complex organ connected with the digestive tract and air passages.

It is advisable that the longitudinal axis of the prosthesis of a vessel be made in the form of a spiral, its coils touching each other to form a cavity whose diameter is essentially the same as that of the organ repaired by the prosthesis.

This construction is acceptable in replacement of a tubular organ after its sleeve resection.

The longitudinal axis of the prosthesis of a vessel must have a wavelike form with the vessel prosthesis branches touching each other.

This construction is used in prosthesis repair of a window defect of a tubular organ.

It is expedient that a prosthesis for a vessel is armored by a framework made of a hemocompatible material chosen from a set consisting of a spiral, ring, half ring and plate.

This construction of the prosthesis provides for maintenance of its shape in response to the pressure of the surrounding tissues. The tubular organ prosthesis for the larynx and trachea, which are anatomically rigid structures, requires a framework made in the form of a spiral.

The framework in the form of a spiral is also applicable for prostheses used for anatomically soft-tissue tubular organs such as the esophagus, bile, urinary ducts and vagina.

In prosthetics for small circular defects of the above tubular organs, use is made of a prosthesis of a tubular organ, in accordance with the invention, with a framework made in the form of a ring or half ring.

In prosthetics for window defects of the larynx and trachea, the framework should have at least one plate to receive pressure arising from the tissues surrounding the prosthesis.

Spiral coils of a prosthesis of a vessel must be interconnected.

Interconnection of the coils is necessary to reproduce the shape of the organ being replaced and, in addition, it facilitates the process of biological mass application on the outer surface of the prosthesis for isolating the cavity from the surrounding medium. Interconnection of the coils can be done by means of sutures either directly through the wall or through the edge made on the surface of the prosthesis of a vessel.

It is necessary to interconnect the branches of the prosthesis of the vessel.

This is accomplished either by sutures or by means of adhesive substances with the result that a "flap" is obtained for repair of a window defect of the tubular organ.

BRIEF DESCRIPTION OF THE DRAWINGS.

Preferred embodiments of the invention will now be described in detail with reference to the accompanying drawings wherein:

FIG. 4 illustrates a prosthesis of the larynx, in accordance with the invention;

FIG. 5 shows a variant of a tubular organ prosthesis used for prosthetics of a window defect of the larynx and trachea;

PREFERRED EMBODIMENT OF THE INVENTION

Figure 1:
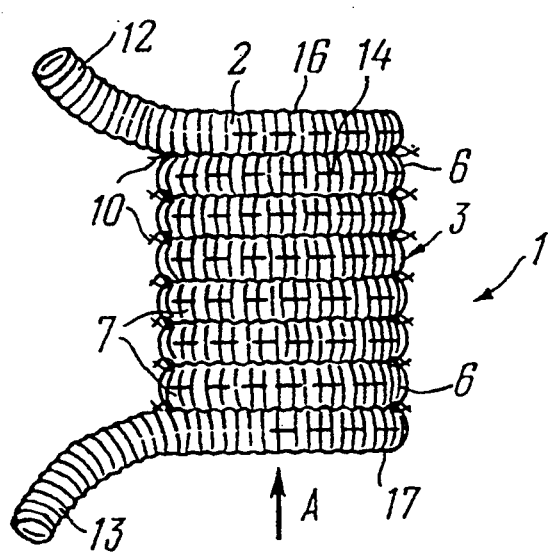
FIG. 1 is a diagram of a front view of a tubular organ prosthesis, in accordance with the invention.
Figure 2:
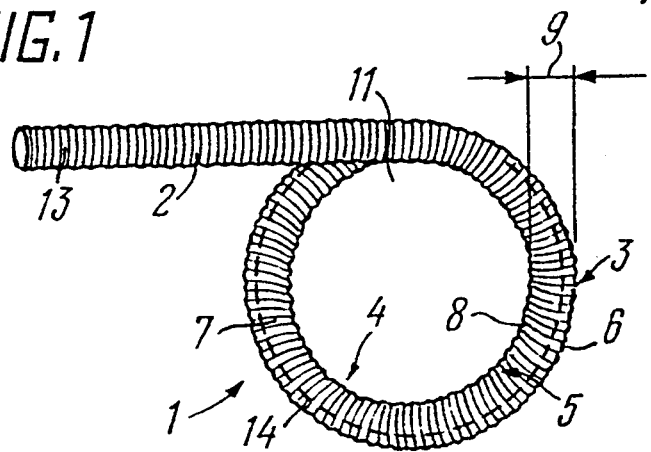
FIG. 2 shows a tubular organ prosthesis, in accordance with the invention, in the direction of arrow A in FIG. 1.

A tubular organ prosthesis 1 (FIG. 1), in accordance with the invention, is made up of a prosthesis of a vessel 2 which forms an outer surface 3 facing tissues and an inner surface 4 (FIG. 2) covered with epithelium of a wall 5 of a tubular organ. The outer surface 3 (FIG. 1) of the prosthesis 1 is a total surface comprising inner surfaces 6 of coils 7 and the inner surface 4 (FIG. 2) of the prosthesis 1 is a total surface of inner surfaces 8 of the coils 7. The prosthesis wall 5 is a sum of walls 9 of each coil 7 of the prosthesis of the vessel 2. The geometric longitudinal axis of the prosthesis 2 (FIG. 1) of the vessel is spiral-shaped. The coils 7 of the prosthesis of the vessel 2 touch each other and are interconnected, e.g., by the interrupted sutures 10 to reproduce the shape of the organ being replaced. The coils 7 make up a cavity 11 (FIG. 2) of the prosthesis 1, the cavity diameter is essentially equal to the inner diameter of the organ repaired by the prosthesis. The cavity 11 is isolated from the surrounding medium by a biological mass, e.g., fibrin glue, applied on the outer surface 3 of the prosthesis 1 at places of connection of the coils 7 (FIG. 1). One end 12 of the prosthesis of the vessel 2 is intended for connection for the period during which the prosthesis of the vessel 2 is filled with blood. A framework 14 made of a hemocompatible material selected from a group consisting of hemotan, biomer, vitur, nitinol, etc., is intended to maintain the shape of the tubular organ prosthesis 1 in response to pressure of the surrounding tissues. The shape of the framework 14 reproduces the shape of a spiral.

The prosthesis 1 of a tubular organ is prepared in the following way.

Figure 3:
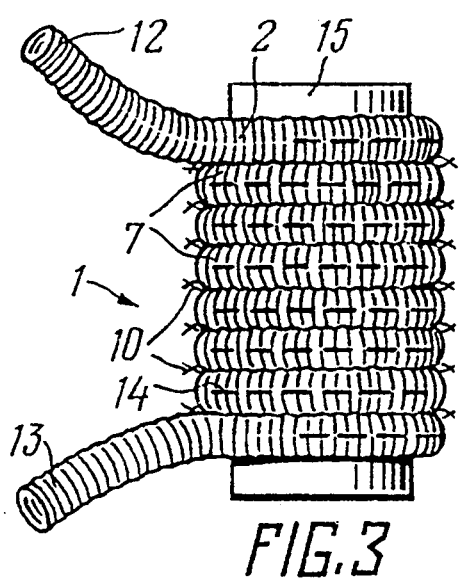
FIG. 3 is a tubular organ prosthesis, in accordance with the invention, fitted on a mandrel rod.

A base in the form of a thread $\Phi$0.3 mm in diameter is used for the framework 14 and coils of the thread are wound on a mandrel rod 15 (FIG. 3) to produce the framework 14 in the form of a spiral. Experimental evidence has confirmed that a thread $\Phi$0.3 mm in diameter imparts the needed rigidity to the prosthesis 1 of a tubular organ. The outer diameter of the mandrel rod corresponds to the diameter of the cavity 11 (FIG. 2) of the prosthesis 1. The mandrel rod 15 (FIG. 3) is cylindrical in shape although it may have a conical shape. One or the other shape of the mandrel rod is determined by the organ repaired with the prosthesis, e.g., prostheses of the larynx, trachea or bronchi are made on a cone-shaped mandrel rod and prostheses of the esophagus, bile and urinary ducts and vagina are prepared on a cylindrical mandrel rod. Threaded on the coils of the framework 14 is the prosthesis of the vessel 2, e.g., made of Lavsan, Teflon, etc. $\Phi$3-5 mm in diameter to obtain the armored prosthesis of the vessel 2 in the form of a spiral with the free ends 12 and 13 of sufficient length for connection with an artery. Then the armored prosthesis of the vessel 2 in the form of a spiral is fitted on the mandrel rod 15. It is common knowledge that a prosthesis for vessels less than $\Phi$3 mm in diameter are often prone to thrombus formation and those more than $\Phi$5 mm in diameter becomes unduly large. Then the coils 7 are fixed relatively to each other, e.g., with the help of the interrupted sutures 10. After that the cavity 11 (FIG. 2) of the tubular organ prosthesis 1 in the form of a spiral is isolated from the surrounding medium by applying biomass, e.g., fibrin glue, along the length of the circumference of the connection of the coils 7 (FIG. 3). The next step consists in the following: one of the ends, e.g., the proximal end 12, is tied up and the distal end 13 is connected with the artery for the tubular organ prosthesis 1 to be filled with blood. After the prosthesis 1 has been filled with blood, the mandrel rod 15 is removed and each end 16 and 17 (FIG. 1), of the prosthesis 1 is connected along the circumference of the coil 7 to the corresponding end of the resectioned tubular organ (not shown in the figures). This is accomplished by applying separate interrupted sutures. In case the proximal end 12 is located in the zone of the artery, it can be connected with the latter.

The results of the experimental and clinical use of the tubular organ prosthesis 1, prepared in accordance with the invention, in prosthetics of the of the larynx, trachea, bronchi, esophagus, bile ducts and vagina are given in the following examples.

EXAMPLE 1

I., a 60 year old male patient. Clinical diagnosis: cancer of the larynx $T_4N_1M_0$. Findings of laryngotracheofibroscopy: tumour of a mixed growth occupies the whole left half of the larynx and spreads to the first tracheal ring. Findings of histological examination: squamous-cell keratinizing carcinoma. An enlarge lymph node up to 20 mm is determined on the left part of the neck (cytologically: cancer metastasis). Operation: orotracheal intubation, narcosis. T-shaped skin incision. Block dissection of the lymph nodes and subcutaneous fat on the left half of the neck with the splenium cervicis muscle and the internal jugular vein— Crile's operation. The larynx with the anterior cervical muscles, left lobe of the thyroid and cervical trachea are isolated from the surrounding tissues. Extensive laryngectomy with resection of five tracheal rings. The pharynx 18 (FIG. 4) is partially sutured so that an orifice is left in its upper part with a diameter of 16 mm. The diastasis between the pharynx 16 and trachea 19 is 80 mm. Diameter of the dissected trachea is 18 mm.

PREPARATION OF THE PROSTHESIS

The mandrel rod (not shown in Fig. ) is selected in the form of a conical tube with diameters of 18 mm and 16 mm and a length of 90 mm. The crimped Lavsan prosthesis of vessel 2 is 400 mm in length and $\Phi 5$ mm in diameter. The framework 14 is prepared from a nitinol thread $\Phi 0.3$ mm in diameter in the form of a spiral with a maximal inner diameter of $\Phi 18$ mm having eight coils. The length of the spiral is 80 mm. The thread of the framework 14 is introduced into the lumen of the prosthesis of the vessel 2 so that its ends 12 and 13 (50 and 70 mm in length) are left free. The armored prosthesis of the vessel 2 is fitted on the mandrel rod (not shown in Fig. ), the coils 7 of the tubular organ prosthesis 1 are fixed between themselves by the separate interrupted sutures 10 (30 sutures). The prosthesis is sealed hermetically by the two-component fibrin glue "BERIPLAST".

INCLUSION OF THE PROSTHESIS INTO THE VASCULAR BED

The proximal end of the prosthesis of the vessel 2 is compressed, its distal end 13 is sutured end to side into the lower third of a left common carotid artery 20. The prosthesis is filled with blood. Its proximal end 12 is sutured end to side in a left external carotid artery 21 in the zone of the origination of a superior thyroid artery 22. Circulation and pulsation of the blood in the prosthesis 1 are adequate, the framework properties are maintained, the prosthesis wall is impermeable to air. The prosthesis 1 removed from the mandrel rod (not shown in Fig. ).

SUTURING OF THE PROSTHESIS

A tracheostoma 23 is applied at a distance of three rings from the end of a trachea 19. The patient is intubated repeatedly, further administration of narcosis through the tracheostoma 23. A pharyngoprosthetic anastomosis 24 with a diameter of $\Phi 16$ mm and the tracheoprosthetic anastomosis with diameter of $\Phi 18$ mm are formed by separate interrupted sutures.

Hemostasis. Layer-by-layer suturing of the wound.

In the postoperative period, feeding is through the gastric tube for 12 days, and breathing is through the tracheostoma. Control X-ray examination within these terms demonstrated good passage of food and the absence of its reflux into the air passages. Endoscopic examination showed good union of the tracheo- and pharyngoprosthetic anastomoses 24 and 25. The inner surface of the wall of the prosthesis 1 is covered with epithelium, the lumen of the whole length of the prosthesis is 12 mm. The cannula is removed. Feeding is through the mouth. One month later a course of radiation therapy was applied on the zone of the primary tumor and metastasis. Treatment is without complications.

The dynamic follow-up 6–8 months later showed that the patient was practically healthy. Breathing is free, swallowing and feeding are normal, voice is preserved. Working capacity is maintained.

EXAMPLE 2

G., a 49 year old male patient. Clinical diagnosis: cancer of the larynx $T_4N_0M_0$, condition after combined treatment: laryngectomy and postoperative radiation therapy, tracheostomy. Posttreatment examination 2 years later showed no progress of the disease. Alloplasty of the larynx was performed.

Operation: T-shaped incision on the neck. Skin flaps were separated, the pharynx was separated, tracheostoma applied. The cervical trachea was separated. The defect in the form of an orifice 20 mm in diameter is formed in the upper third of the pharynx. The diastasis between the trachea and pharynx is 60 mm, tracheal diameter is 16 mm.

Prosthesis of the larynx was prepared according to the techniques indicated in Example 1 and FIG. 4.

Examination 9 months later showed that the patient was practically healthy. Full epithelization of the prosthesis, breathing is free, the act of swallowing is normal. The inner diameter of the prosthesis of the nasopharynx is $\Phi 12$ mm.

EXAMPLE 3

I., a 57 year old female patient. Clinical diagnosis: cicatricial post-traumatic stenosis of the larynx and trachea. Condition after repeated surgical interventions. Laryngotracheostoma.

Operation: alloplasty of laryngotracheostoma.

Orotracheal intubation. Longitudinal cervicotomy with edging and separating of the stoma edges. The stoma dimensions (length and width) 40×25 mm. The stoma is surrounded by cicatricial tissues. The left common carotid artery is separated.

PREPARATION OF THE PROSTHESIS

The crimped prosthesis of the vessel 2 (FIG. 5) (diameter Φ5 mm, length 300 mm) is given a wave-like (six coils) leaving its end 12a, 13a free (length to 50 mm) on each side. Prosthesis branches 7a touching each other are connected with the help of interrupted sutures 10a, e.g., 30 sutures. A flap is prepared equal to a stoma 26. Biomass, e.g., fibrin glue, is applied to the outer surface of the flap along the suture line. In this way the tubular organ prosthesis is prepared in the form of a flap. To lessen pressure exerted by tissues on the prosthesis 1a it is armored in the framework which comprises two plates 27 made of hemotan (the size of each plate is 45×30 mm, thickness 2 mm). The plates 27 are located on the outer surface of the prosthesis 1a and are connected with it by sutures 28 (12 sutures).

The prosthesis 1a is included in the vascular bed in the same way as indicated in Example 1. The difference lies in the fact that the proximal end 12a is tied up.

SUTURING OF THE PROSTHESIS

The separate interrupted sutures 29 are used to unite the prosthesis 1a in the form of a flap along the perimeter of the stoma 26 with its edges by 20 sutures. The wound is sutured layer by layer. The postoperative period is uneventful. Examination after 9 months: the patient is healthy; endoscopic findings: the prosthesis is epithelialized; breathing is free; working capacity is preserved.

EXAMPLE 4

E., a 60 year old female patient. Clinical diagnosis: cancer of the trachea. Findings of roentgenoendoscopy: the tumour is determined beginning with the fourth cartilaginous semiring of the trachea predominantly along its left and anterior wall. It narrows the organ lumen up to 5 mm. The lesion is 80 mm in length. Histological findings: squamous-cell carcinoma.

Operation: resection of the trachea with alloplasty. Partial lengthwise transverse sternotomy. The cervical and thoracic tracheal segments are separated. Sleeve resection of the trachea (12 rings) is performed. The diastasis between the resectioned tracheal ends after their pulling is 50 mm. No possibility to establish direct anastomosis between the ends. Diameter of the proximal tracheal half ring is Φ18 mm, that of the distal tracheal half ring Φ14 mm.

PREPARATION OF THE PROSTHESIS

Prosthetics of the trachea is accomplished in accordance with FIG. 4. The prosthesis is prepared in the same way as described in Example 1. The differences are as follows: dimensions of the mandrel rod (diameters 18 and 14 mm and length 100 mm); dimensions of the framework which is made in the form of a spiral having nine coils (inner diameter 16 mm, length 85 mm); the length of the free ends (70 mm and 20 mm).

INCLUSION OF THE PROSTHESIS IN THE VASCULAR BED

The distal end of the prosthesis of the vessel is compressed. Its proximal end is sutured in the lower third of the left common carotid artery end to side. Pulsation of the prosthesis is good, its wall is impermeable to air. The prosthesis is removed from the mandrel rod.

SUTURING OF THE PROSTHESIS

Orotracheal intubation is achieved by advancing the tube through the prosthesis. The proximal and distal tracheoprosthetic anastomoses are created by separate interrupted sutures. The would is drained and sutured tightly. The postoperative course is smooth. The patient is discharged on the 16th day. Examination one month postoperatively. The prosthesis is epithelialized; the course of radiation therapy is carried out. Post-treatment examination 6 and 9 months later: the patient is practically healthy.

EXAMPLE 5

S., a 60 year old male patient. Clinical diagnosis: cancer of the upper lobe of the left lung $T_3N_2M_0$. Findings of roentgenoendoscopy: atelectasis of the right lung, the tumour obstructs the intermediate, upper-lobe and right main bronchi, spreads to the bifurcation segment and five rings of the thoracic trachea. The ostium of the left main bronchus is unobstructed. Metastatic involvement of the paratracheal and bifurcation lymph nodes. Histological findings: squamous-cell keratinizing carcinoma.

Figure 6:
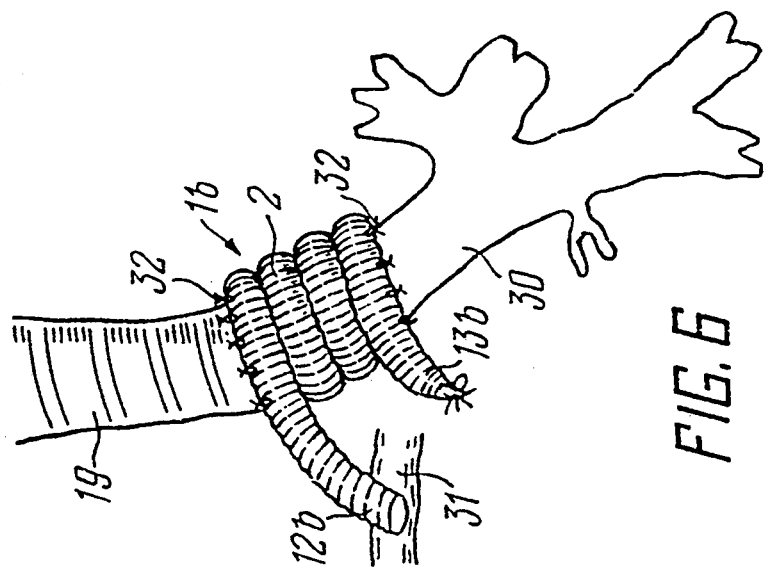
FIG. 6 is a tracheobronchial prosthesis, in accordance with the invention.

Operation: anterolateral thoracotomy in the fifth intercostal space on the right. The lung is in a state of atelectasis, the tumour is 12 cm in diameter and occupies the upper lobe; a conglomeration of the enlarged paratracheal and bifurcation lymph nodes is found. Resection involved the right lung, main bronchus, tracheal bifurcation, ring of the left main bronchus, seven rings of the thoracic trachea and paratracheal and bifurcation lymph nodes. The diastasis between the dissected ring 30 (FIG. 6) of the left main bronchus (diameter 12 mm) and the resectioned tracheal end 19 (diameter 16 mm) is 60 mm.

PREPARATION OF THE PROSTHESIS

The prosthesis is prepared in the same way (FIG. 1) as described in Example 1. The differences are as follows: dimensions of the mandrel rod (diameter 14 mm, length 70 mm); dimensions of the framework made in the form of a spiral having nine coils; length of the vessel free ends (length 50 and 10 mm).

INCLUSION OF THE PROSTHESIS IN THE VASCULAR BED

A free end 13b (length 10 mm) of the prosthesis of the vessel is tied up and the other free end 12b of the prosthesis of the vessel 2 is anastomosed end to side with the right branch of the pulmonary artery 3. Pulsation of the prosthesis 16 is normal. The outer surface of the wall of the prosthesis 16 is airtight. The prosthesis is removed from the mandrel rod.

SUTURING OF THE PROSTHESIS

The tracheo- and bronchoprosthetic anastomoses are created by separate interrupted sutures 32. Fibrin glue is additionally applied to the suture line of the anastomoses. The pleural cavity is drained and the wound sutured. The postoperative period is uneventful. Breathing is free. Radiation therapy was carried out 1 month postoperatively.

Examination after 6 to 9 months showed that the patient was practically healthy.

EXAMPLE 6

S., a 55 year old male patient. Clinical diagnosis: cancer of the tracheal bifurcation with involvement of the thoracic trachea. Findings of roentgenoendoscopy: the tumor occupies the posterior and right wall of the tracheal bifurcation and spreads to five rings of the thoracic trachea. Histological findings: squamous-cell carcinoma.

Operation: posterior thoracotomy of the right in the further intercostal space. The bifurcation and thoracic segments of the trachea are separated. Resection of the tracheal bifurcation was performed at the level of the ostia of the main bronchi and thoracic trachea involving eight rings. The defect 40 mm in length formed between the ostia of the main bronchi and trachea. The right main bronchus was 10 mm, the left main bronchus 12 mm and the trachea 16 mm in diameter.

PREPARATION OF THE PROSTHESIS

Figure 7:
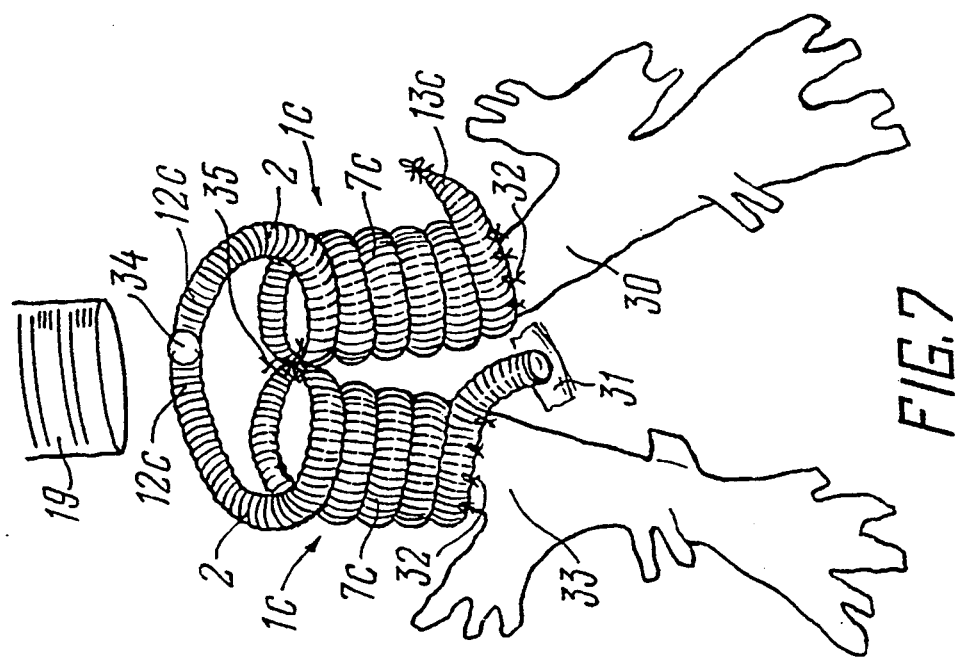
FIG. 7 is a bronchial prosthesis, in accordance with the invention.

Two similar prostheses 1c (FIG. 7) are required to repair the bronchial and tracheal fragments. Each of the prostheses 1c is prepared in the same way as described in Example 1. The differences are as follows: dimensions of the mandrel rod (diameter $\Phi 10$ mm, length 50 mm); dimensions of the framework made in the form of a six coil spiral; dimension of the free ends of the prosthesis of the vessel; each end is 30 mm in length.

INCLUSION OF THE PROSTHESIS IN THE VASCULAR BED

The end-to-end anastomosis 34 is created by connecting the proximal ends 12 of each prosthesis of the vessel 2 between themselves for connecting both prostheses 1c with the trachea 19.

The distal end 13c of the prosthesis of the vessel 2 of the left prosthesis of the bronchus 1c is tied up and the distal end 13c of the prosthesis of the vessel 2 of the right prosthesis 1c of the bronchus is anastomosed end to side with the right branch of the pulmonary artery 31. Pulsation of the prosthesis is adequate, the outer surface of the wall of each prosthesis is impermeable to air. The prostheses are removed from the mandrel rod.

SUTURING OF THE PROSTHESES

The distal end 13 of each bronchial prosthesis 1c is anastomosed with a resected end of a corresponding right bronchus 33 and left bronchus 30, i.e., bronchoprosthetic anastomoses 32 are established. The proximal end 12c of one prosthesis 1c of the trachea is sutured with the proximal end 12c of the other prosthesis 1c of the trachea 19 and in the middle zone of the first 35 coils 7c by the type of a "double-barreled gun" (not shown in Fig. ), which is sutured along the whole perimeter in the resected part of the trachea 19. Then fibrin glue is applied on the suture line of the anastomoses.

The operative wound is drained and sutured tightly. The patient was discharged on the 19th day. Both prostheses are fully covered with epithelium. The course of radiation therapy was carried out one month postoperatively. Examination finding after 6 to 10 months: the patient is practically healthy.

EXAMPLE 7

Sh., a 55 year old male patient. Clinical diagnosis: cancer of the tracheal bifurcation with involvement of the thoracic segment and main bronchi. Findings of roentgenoendoscopy: the tumor occupies the anterior and left walls of the tracheal bifurcation, 8 mm of the main bronchi and spreads to eight rings of the thoracic trachea. Histological findings: squamous cell carcinoma.

Operation: posterior thoracotomy on the right in the fourth intercostal space. Resection of the tracheal bifurcation with segments, including two rings of the main bronchi and ten rings of the thoracic trachea. The diastasis between the resectioned bronchial and tracheal ends is 90 mm. Each resectioned end of the main right bronchus is 10 mm, of the left 12 mm and of the trachea 18 mm in diameter.

PREPARATION OF THE PROSTHESES

Figure 8:
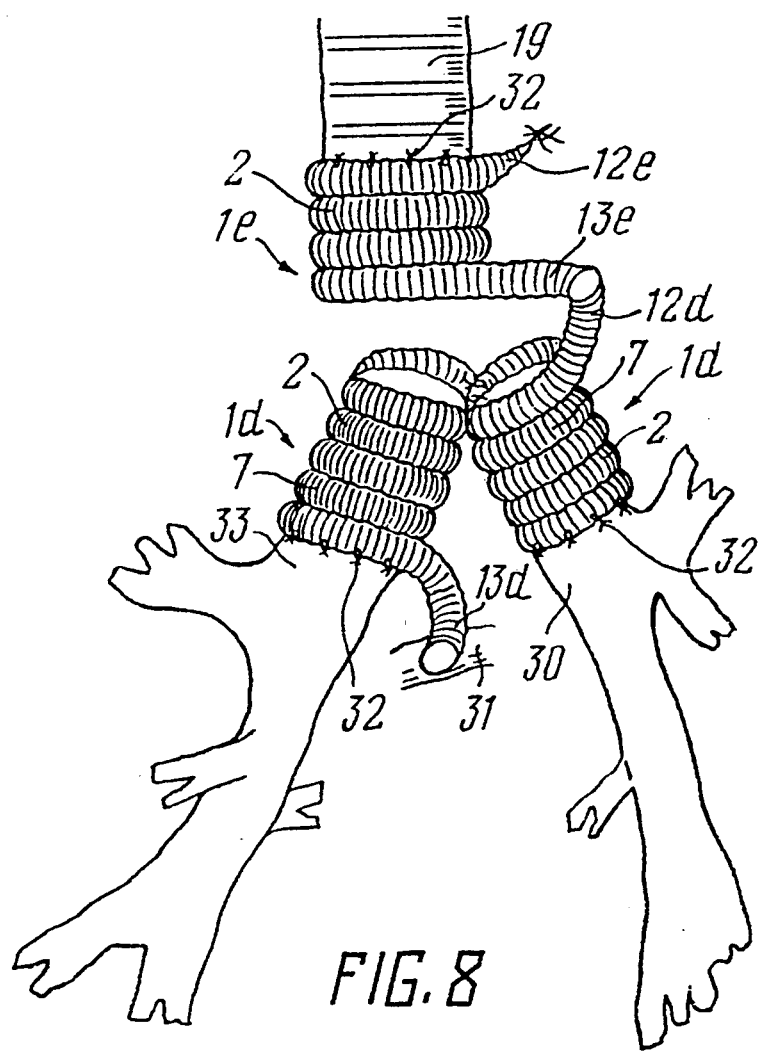
FIG. 8 are bronchial and tracheal prostheses, in accordance with the invention.

Prostheses 1d and 1e (FIG. 8) to repair a left bronchus 33 and a right bronchus 30 of the main bronchi are prepared in the same way as indicated in Example 8. The tracheal prosthesis 1e is prepared similarly to that described in Example 1. The differences in the mandrel rod dimensions: diameter $\Phi 18$ mm, length 40 mm.

The prostheses 1d and 1e are included in the vascular bed in the same way as described in Example 8. Differences concern connection of the prostheses 1d and 1e between themselves, i.e., the proximal end (not shown in Fig. ) of the prosthesis of the vessel 2 of the right prosthesis 1d of the bronchus is connected with the distal end (not shown in Fig. ) of the prosthesis of the vessel 2 of the left prosthesis 1d of the bronchus, the proximal end 12d of the prosthesis of the vessel 2 is connected with the distal end 13e of the prosthesis of the vessel 2 of the prosthesis 1e of the trachea and the proximal end 12e of the prosthesis of the vessel 2 is tied up.

Suturing of the prosthesis 1d of the bronchi is the same as described in Example 6, suturing of the tracheal prosthesis 1e is the same as that described in Example 5. The differences consist in that the prosthesis 1e of the trachea is anastomosed with the prosthesis 1d of the bronchi by the type of a "double barreled gun".

The wound is drained and is closed tightly. The patient was discharged on the 20th day. The prostheses were epithelialized. A course of radiation therapy was conducted on month postoperatively. Examination findings after 6.5 months: the patient was practically healthy.

It follows from the examples described above that the tubular organ prostheses prepared in accordance with the invention proved to be effective in repair of the larynx, trachea and bronchi. Use of the proposed prosthesis is not only for repair of the above organs. It can be used successfully for prosthetics of the tubular organs such as esophagus, bile and urinary ducts and vagina.

EXAMPLE 8

E., a 50 year old female patient. Clinical diagnosis: cancer of the choledochus, obstructive jaundice.

Operation: laparotomy. The duodenum and choledochus were separated. Affection of the choledochus was found at the level of the cystic duct. The lesion was 50 mm in length.

Choledochotomy and cholecystectomy were performed. The resected choledochus was $\Phi 10$ mm in diameter, the diastasis between its end was 60 mm. Repair of the choledochus with the prosthesis prepared in accordance with the invention is that described in Example 1. The difference consists in creation of the anastomosis between the distal end of the prosthesis of the vessel of the prosthesis of the choledochus and the abdominal aorta and typing up of the proximal end. The patient was examined after 3 months. There were no signs of jaundice.

EXAMPLE 9

S., a 60 year old male patient. Clinical diagnosis: cancer of the cervical portion of the esophagus with involvement of the laryngopharynx. Findings of roentgenoendoscopy: lesion of the cervical portion of the esophagus 1.5 cm in length with infiltration of the pharyngoesophageal ring.

Operation: lengthwise cervicotomy with separation of the cervical portion of the esophagus and larynx. Sleeve resection of the esophagus 40 mm in length and laryngopharynx 10 mm in length were performed. The diastasis between the resected organs was 30 mm.

Repair of the esophagus and laryngopharynx with the prosthesis made in accordance with the invention in that described in Example 1. The difference consists in that the part of the prosthesis that replaces the laryngopharynx with two coils in length was not armored due to the anatomical features of the organ being repaired.

Examination after 6 months showed that the patient was practically healthy, eating was normal.

EXAMPLE 10

E., a 40 year old female patient. Clinical diagnosis: cicatricial stenosis of the middle third of the ureter on the left 50 mm in length.

Operation: the lumbus was incised on the left. Resection of its affected part. The diastasis between the resected ends of the ureter was 40 mm in length. The ureter was repaired with the prosthesis made in accordance with the invention in the same was as described in Example 1. The difference is that the proximal and distal ends of the prosthesis of the vessel of the prosthesis of the ureter are anastomosed in the abdominal aorta. Examination after 6 months showed that the patient was practically healthy.

EXAMPLE 11

S., a 46 year old female patient. Clinical diagnosis: cancer of the cervix uteri, condition after radiation therapy, continuous growth with involvement of the vagina.

Operation: Wertheim's operation with removal of the vagina leaving its fragment 15 mm in length.

Repair of the vagina with the prosthesis made in accordance with the invention is that described in Example 1. The difference is that the proximal end of the prosthesis of the vessel of the prosthesis of the vagina is anastomosed in the left internal iliac artery and the distal end of the prosthesis of the vessel is tied up.

Examination after 6 months showed that the patient was practically healthy.

INDUSTRIAL APPLICABILITY

The tubular organ prosthesis prepared in accordance with the invention can be used in prosthetics of an organ as a whole, e.g., larynx, trachea, bronchus, bile and urinary ducts, esophagus, vagina and in repair of window defects of the above tubular organs. The given construction of the prosthesis provides for continuous blood flow in it to promote epithelization of the inner wall of the prosthesis. The latter circumstance prevents development of cicatricial granulation changes in the zone of the anastomosis and prosthesis.

I claim:

1. A prosthesis for replacing a portion of a tubular organ of a patient through which blood circulates comprising:
a tubular vessel in the form of a coiled spring, coils thereof being formed by coiling said prosthesis into the shape of a coiled spring with said coils touching each other, and having a length substantially equal to a length of the tubular organ to be replaced, wherein a wall of said prosthesis of the tubular organ is defined by said coils touching each other and having an outer surface adapted to face surrounding tissues and an inner surface adapted to be covered with epithelial surface defining a cavity having a diameter substantially equal to an inner diameter of the tubular organ, wherein said prosthesis has two free ends, a first of said free ends adapted for connecting with an artery of a vascular system of the patient for filling said prosthesis with blood and a second of said free ends adapted for compressing during filling said vessel with blood, thereby providing a tubular organ prosthesis adapted to be connected to the vascular system of the patient, with said inner surface facilitating the formation of an epithelial surface covering thereon.

2. A prosthesis for a tubular organ according to claim 1, comprising:
a framework made of a hemocompatible material for retaining the shape of the tubular organ when the tubular organ is acted upon by a force from the direction of the surrounding tissues; and
an element in the form of a coiled spring forming said framework accommodated in said coils of said prosthesis.

3. A prosthesis for a tubular organ prosthesis according to claim 2, wherein said coils of said prosthesis are interconnected.

4. A prosthesis according to claim 1, wherein said vessel comprises a framework of a hemocompatible material for retaining the shape of a coiled spring when subjected to force by the surrounding tissues.

5. A prosthesis according to claim 4, wherein said framework further comprises a wire member in the form of a cylindrical spiral forming said framework.

6. A prosthesis for replacing a portion of a tubular organ of a patient through which blood circulates comprising:
a vessel folded to the form of a sine curve, branches of said vessel being folded to fit the form of a sine curve, touching one another, and having a length substantially equal to a length of the tubular organ to be replaced, a wall defined by said branches touching one another, and having an outer surface adapted to be facing tissues and an inner surface adapted to be covered with an epithelial surface defining the cavity of the tubular organ; and
two free ends of said prosthesis, a first of said free ends adapted for connecting with an artery of a vascular system of the patient for filling said prosthesis with blood and a second of said free ends adapted for compressing during filling said vessel with blood, thereby providing a tubular organ prosthesis adapted to be connected to the vascular system of the patient, with said inner surface facilitating the formation of an epithelial surface covering thereon.

7. A prosthesis for a tubular organ according to claim 6, wherein said branches are interconnected.

8. A prosthesis for a tubular organ according to claim 7, comprising:

a framework made of a hemocompatible material for retaining the shape of the tubular organ when the tubular organ is acted upon by a force from the direction of the surrounding tissues; and a laminar element forming said framework, disposed on said outer surface and connected with said vessel prosthesis.

* * * * *